United States Patent [19]

Stüber

[11] Patent Number: 5,049,506

[45] Date of Patent: Sep. 17, 1991

[54] PROLINE-CONTAINING DECAPEPTIDES AS SUBSTRATES FOR FACTOR XIII

[75] Inventor: Werner, Stüber, Lahntal, Fed. Rep. of Germany

[73] Assignee: Behringwerke Aktiengesellschaft, Marburg/Lahn, Fed. Rep. of Germany

[21] Appl. No.: 263,158

[22] Filed: Oct. 27, 1988

[30] Foreign Application Priority Data

Oct. 29, 1987 [DE] Fed. Rep. of Germany ....... 3736589

[51] Int. Cl.$^5$ .................... G01N 33/86; C07K 7/06
[52] U.S. Cl. .................................. 436/69; 530/328
[58] Field of Search .................. 436/69; 530/328, 335, 530/338

[56] References Cited

FOREIGN PATENT DOCUMENTS 0155199 9/1987 European Pat. Off. .

OTHER PUBLICATIONS

Gorman & Folk, *J. Biol. Chem.* 259(14), 1984, pp. 9007–9010.
Poulson et al., ed. *Organic Chemistry*, 1980, pp. 1025–1031.
Chemical Abstract, vol. 100, 1984, p. 619, Abstract No. 192243j, Columbus, Ohio, U.S.
Fesus et al., Clin. Chem., vol. 31, No. 12, pp. 2044–2045, published 1985.
Muszbek et al., Clin. Chem., vol. 31, No. 12, pp. 35–40, published 1985.

*Primary Examiner*—Lester L. Lee
*Assistant Examiner*—Stephen B. Maebius
*Attorney, Agent, or Firm*—Finnegan, Henderson, Farabow, Garrett, and Dunner

[57] ABSTRACT

Glutamine-containing peptides, a process for the preparation thereof, and the use thereof Peptides of the structure

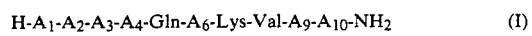

$$H\text{-}A_1\text{-}A_2\text{-}A_3\text{-}A_4\text{-}Gln\text{-}A_6\text{-}Lys\text{-}Val\text{-}A_9\text{-}A_{10}\text{-}NH_2 \quad (I)$$

in which $A_1 =$ Val, Leu
$A_2 =$ Gly, Ser
$A_3 =$ Pro, Hyp
$A_4 =$ Gly, Ser
$A_6 =$ Gly, Ser
$A_9 =$ Leu, Ile and
$A_{10} =$ Gly, Ala, and the salts thereof, and a process for the preparation thereof, are described. These peptides act as substrates of blood coagulation factor XIII and can be used for the quantification of this enzyme and for detecting reactions in which activated blood coagulation factor XIII is produced, consumed or inhibited.

7 Claims, No Drawings

PROLINE-CONTAINING DECAPEPTIDES AS SUBSTRATES FOR FACTOR XIII

The invention relates to peptides of the structure

H-A$_1$-A$_2$-A$_3$-A$_4$-Gln-A$_6$-Lys-Val-A$_9$-A$_{10}$-NH$_2$     (I)

in which A$_1$ = Val, Leu
A$_2$ = Gly, Ser
A$_3$ = Pro, Hyp
A$_4$ = Gly, Ser
A$_6$ = Gly, Ser
A$_9$ = Leu, Ile and
A$_{10}$ = Gly, Ala,
and the salts thereof, to a process for the preparation thereof, and to the use thereof. These peptides act as substrates of blood coagulation factor XIII and can be used for the quantification of this enzyme and for detecting reactions in which activated blood coagulation factor XIII is produced, consumed or inhibited.

The present invention is based on the mode of action of the transglutaminase F XIII which brings about, in various physiological processes, the incorporation of primary amines into proteins which possess the amino acid glutamine as amine acceptor. In this reaction, which in the framework of blood coagulation brings about the production of an insoluble blood clot, ammonia is formed as byproduct. There are methods which allow the F XIII concentration in a sample to be determined from a subsequent measurement of ammonia. For example, the ammonia which is produced continuously by the F XIII-mediated incorporation of ethylamine into acetylated β-casein can be measured by an NADH reaction. In this NADH reaction the ammonia which is produced is incorporated under the action of the enzyme GLDH into alpha-ketoglutarate. This results in the production of glutamic acid and, at the same time, NADH is consumed with the formation of NAD$^+$. Since the NADH and NAD$^+$ differ distinctly in spectral behavior, a measurement of the decrease in extinction, for example at 340 nm, yields the change in ammonia concentration, and the F XIII concentration is determined from these kinetics.

This disadvantage of this method is that the substrate used is casein, specifically β-casein, which has to be dephosphorylated and N-acetylated. Since only one glutamine in the protein structure is used for amine incorporation, relatively high substrate concentrations are required. It is reported in Clin. Chem. 31/12, 2044–2045, 1985, that the use of certain glutamine-containing peptides improves these disadvantages since unambiguously defined substrates are offered to the F XIII. The suitability of such peptide substrates can be determined from the kinetic behavior, that is to say from the rate of change of optical density (delta OD/time), with, of course, high values being favorable in order to be able to determine with sufficient accuracy even relatively low concentrations of F XIII.

The object of this invention was to provide glutamine-containing peptides having properties superior to those of the said state of the art, that is to say high conversion rates and thus high delta OD/time values.

It has now been found, surprisingly, that peptides of the abovementioned structure I meet this condition in a particularly suitable manner. An essential difference from the state of the art, and thus the novelty, is provided by the presence of proline or hydroxyproline in the 3 position.

Hence the invention relates to peptides of the structure indicated above in formula I with the relevant definitions.

The amino acids used for constructing the peptides can be both in the D and in the L form, but the L form is preferred. It proves to be beneficial to incorporate a D-amino acid at the N-terminus, because this is able to prevent undesired enzymatic degradation of the substrate.

Particularly suitable are the following peptides (in general, the amino acids are in the L form unless otherwise noted):

H-Leu-Gly-Pro-Gly-Gln-Gly-Lys-Val-Leu-Gly-NH$_2$

H-Leu-Gly-Hyp-Gly-Gln-Gly-Lys-Val-Leu-Gly-NH$_2$

H-Leu-Gly-Pro-Gly-Gln-Ser-Lys-Val-Leu-Gly-NH$_2$

H-Leu-Gly-Hyp-Gly-Gln-Ser-Lys-Val-Leu-Gly-NH$_2$

H-Leu-Ser-Pro-Ser-Gln-Ser-Lys-Val-Leu-Gly-NH$_2$

H-Leu-Ser-Hyp-Ser-Gln-Ser-Lys-Val-Leu-Gly-NH$_2$

H-Leu-Gly-Pro-Gly-Gln-Ser-Lys-Val-Ile-Gly-NH$_2$

H-D-Leu-Gly-Pro-Gly-Gln-Ser-Lys-Val-Ile-Gly-NH$_2$

H-D-Leu-Gly-Pro-Gly-Gln-Ser-Lys-Val-Leu-Gly-NH$_2$

In this connection, the peptides according to the invention can be in the form of their salts, for example as chlorides, acetates, formates, bromides or methanesulfonates.

These peptides can be prepared by processes known per se, for example by the classical technique working in solution, where individual protected amino acids or else peptide segments are condensed together and the desired peptide is obtained after elimination of the protective groups. Examples of protective groups used for the alphaamino group for this purpose are Boc, Z, Ddz, Bpoc or Fmoc (see hereinafter for abbreviations). Used as side-chain protective groups for lysine are Boc, Z, o-ClZ, o-BrZ or TFA, and for serine are Bzl or t-Bu.

It is suitable and preferred to use for the preparation of the peptides according to the invention peptide segments which are then used to construct the final sequences. It has proved beneficial to couple the peptide segment A$_1$-A$_2$-A$_3$-A$_4$ to the segment Gln-A$_6$-Lys-Val-A$_9$-A$_{10}$-NH$_2$. The amino group of A$_1$ must be provided with a protective group with, in accordance with the above statement, Boc or Z being very particularly preferred. If A$_3$ is hydroxyproline, the t-Bu group on the hydroxyl group proves advantageous. The epsilon-amino group of the C-terminal hexapeptide is likewise protected. The individual peptide segments mentioned here are constructed using individual protected amino acids in solution, with suitable and preferred solvents being such as dimethylformamide, N-methylpyrrolidone and dimethyl sulfoxide. The carboxyl group activation steps are preferably carried out with a carbodiimide, particularly preferably dicyclohexylcarbodiimide, in the presence of hydroxybenzotriazole or hydroxysuccinimide. The pH values are maintained in the range 4 to 10 in the coupling steps, with a base such as N-methylmorpholine preferably being used, so that a pH of 6 to 8 results. The individual peptide segments, as well as the protected decapeptides, are purified by known methods. The peptides are preferably dissolved in organic solvents which are known to be suitable as solvents for peptides, for example ethyl acetate or butanol, and are not completely miscible with water, and the peptide solutions are washed with water, 1M potassium bisulfate and 1M sodium bisulfate. The peptides according to the invention, corresponding to formula (I), are preferably purified by gel permeation chromatography, preferably on $^R$Sephadex G25 using 1% strength (Vol.) acetic acid.

In addition, the solid-phase method is suitable for the preparation of the peptides according to the invention. This entails the peptides being constructed on a matrix such as crosslinked polystyrene, polyacrylamide or the like, which are provided with appropriate anchors, and selectively eliminated therefrom.

Thus the invention also relates to a process for the preparation of the peptides according to the invention by the solid-phase technique of peptide synthesis. According to the state of the art, the solid phases must be provided with so-called anchor molecules which allow elimination of the peptides in the form of their amide derivatives. Examples of such anchor compounds are immobilized benzhydrylamine derivatives, to which the first amino acid in the sequence is then coupled. The solvent preferably used for this purpose is dichloromethane, N-methylpyrrolidone and, very particularly preferably, dimethylformamide. The amino acids are activated, for example, via active esters, mixed or symmetric anhydrides or carbodiimide activations. The peptides are eliminated from the support preferably by acidolysis, with simultaneous removal of the side-chain protective groups. The peptides are then purified by methods known per se, particularly preferably by gel permeation chromatography.

The use of crosslinked amino-functionalized polystyrene (1 g of crosslinker per 100 g of polystyrene) is preferred for the solid-phase peptide synthesis. The C-terminal amino acid is particularly preferably coupled to the polymeric support via benzhydrylamine derivatives, with Fmoc-amino acid (4-carboxymethoxyphenyl-4-methoxyphenyl)-methylamide being very particularly preferably bound to amino groups of the matrix via a carbodiimide-mediated reaction.

After elimination of the Fmoc group and DMF-isopropanol washing steps, the protected amino acid which follows in the sequence is added in 3-fold molar excess based on the amount of amino groups detectable on the solid phase, as well as a 4.5-fold excess of HOBt. Addition of a 3.3- fold excess (based on the amino groups) of diisopropylcarbodiimide or dicyclohexylcarbodiimide is followed by the coupling being carried out for one hour. Subsequently excess reagents are removed by washing with DMF and isopropanol.

The peptides according to the invention are eliminated from the solid phase by an acidolytic treatment, preferably with a mixture of 4 parts by volume of trifluoroacetic acid and one part by volume of a 3:1 (v:v) mixture of methyl phenyl sulfide and dimercaptoethane. The crude peptides are precipitated by addition of ether, preferably diethyl ether, and purified by customary purification steps which are known per se. Preferred are ion exchange chromatography or gel permeation, for example on $^R$Sephadex G-25 with 0.5ml/100ml acetic acid as eluent.

To test the peptides for their suitability as substrates for the transglutaminase F XIII, a sample solution which contains factor XIII is activated in a buffer mixture which contains about 30mmol/l calcium chloride at pH 7.6±0.5 with thrombin. The peptide solutions, a solution of an amine derivative, for example glycine ethyl ester or glycine methyl ester, ketoglutarate buffer, glutamic dehydrogenase and an NADH solution are then added. The liberation of ammonia from the decapeptide amide is then measured by means of the decrease in extinction at 340±15nm, and the activity of F XIII is determined.

It has been established, surprisingly, that the peptides according to the invention are very suitable for detecting F XIII. It is important that these peptides have as $A_3$, in the formula proline or a related amino acid, for example hydroxyproline. It was possible, surprisingly, to show in comparative investigations that the rate of cleavage, measured as the change in extinction per unit time, is greater than with known substances.

Hence it is possible with these substrates to reduce the detection limit for F XIII and to achieve greater accuracy of measurement. Hence the invention also relates to the use of peptides of the formula I in a method for the determination of glutaminases, preferably F XIII.

The Examples which follow describe the invention in more detail:

EXAMPLE 1

Synthesis of
H-Leu-Gly-Pro-Gly-Gln-Gly-Lys-Val-Leu-Gly-NH$_2$ 1 g of aminomethylpolystyrene (1 g/100 g crosslinker; 0.49 mmol NH$_2$ groups/g) were swollen in 15 ml of DMF and reacted in a $^R$Labortec AG SP 640 peptide synthesizer. Starting with the C-terminal amino acid and after the customary resin washing steps, 1.5 mmol of Fmoc-glycine (4-carboxymethoxyphenyl-4-methoxyphenyl)methylamide and 2.25 mmol of HOBt dissolved in 15 ml of DMF were added to the resin and activated with 1.65 mmol of diisopropylcarbodiimide. The reaction mixture was shaken at room temperature for one hour and then excess reagents and by-products were removed from the polymer by washing steps with DMF and isopropanol. The Fmoc protective group was eliminated by reaction for 10 minutes with a 20 ml/100 ml piperidine solution in DMF.

This reaction cycle was maintained up to the N-terminal amino acid. The following amino acid derivatives were used: Fmoc-Leu, Fmoc-Val, Fmoc-Lys (Boc), Fmoc-Gly, Fmoc-Gln, Fmoc-Pro, Boc-Leu (N-terminal amino acid).

The peptide-polymer was treated with 16 ml of TFA, 3 ml of thioanisole and 1 ml of ethanedithiol at 35° C. for 2 hours. The peptide-containing solution was filtered and then diethyl ether was added, and the crystalline peptide was filtered off and dried. The crude peptide was dissolved in 20 ml of 0.5 ml/100 ml acetic acid and purified in a $^R$Sephadex G-25 column. The peptide fraction was freeze-dried. Yield: 370 mg.

EXAMPLE 2

Synthesis of H-Leu-Ser-Hyp-Ser-Gln-Ser-Lys-Val-Leu-Gly-NH₂

This peptide was constructed in analogy to Example 1 with the same amino acid derivatives with the exception of Fmoc-Ser(tBu) and Fmoc-Hyp(tBu). The working steps and quantity data correspond to Example 1.

The other peptides are synthesized analogously.

EXAMPLE 3

Determination of factor XIII activity by photometric measurement

50 μl of a solution containing factor XIII (0.6 U), which had been adjusted to pH 7.6 and which contained 50 millimolar HEPES, 150 milli molar sodium chloride and 30 millimolar $CaCl_2$, were incubated with 25 μl of thrombin solution (30 units dissolved in 1 ml physiological saline) in a 1 ml cuvette at 37° C. for 10 min. 700 μl of a buffer solution composed of triethanolamine pH 8.0, 2.2 g of alpha-ketoglutarate/liter and 133 mg of NADH/liter were added. The sample solution was then mixed with 25 μl of a solution of 5 ml of glutamic dehydrogenase (about 120 units/mg), 100 ml of glycerol, pH 7, 100 μl of glycine ethyl ester (30 mg/ml in $H_2O$) and 100 μl of decapeptide amide solution (10 mg/ml in $H_2O$). The decrease in extinction was measured. The results of the kinetic measurement at 340 nm are to be found in the form of delta OD/min values in the following Tables.

| Peptide sequence | Delta OD/min |
| --- | --- |
| Leu—Ser—Leu—Ser—Gln—Ser—Lys—Val—Leu—Gly—NH₂ | 0.21 |
| Leu—Gly—Gly—Gly—Gln—Gly—Lys—Val—Leu—Gly—NH₂ | 0.12 |
| Leu—Gly—Pro—Gly—Gln—Ser—Lys—Val—Leu—Gly—NH₂ | 0.32 |
| Leu—Gly—Hyp—Gly—Gln—Ser—Lys—Val—Leu—Gly—NH₂ | 0.27 |
| Leu—Gly—Pro—Gly—Gln—Ser—Lys—Val—Ile—Gly—NH₂ | 0.35 |

Abbreviations

NADH Nicotinamide-adenine dinucleotide, reduced
NAD+ Nicotinamide-adenine dinucleotide
GLDH Glutamic dehydrogenase
nm Nanometers
Val Valine
Leu Leucine
Gly Glycine
Ser Serine
Pro Proline
Hyp Hydroxyproline
Ile Isoleucine
Ala Alanine
Gln Glutamine
Lys Lysine
Boc tert.-Butyloxycarbonyl
Z Benzyloxycarbonyl
o-ClZ o-Chlorobenzyloxycarbonyl
o-BrZ o-Bromobenzyloxycarbonyl
TFA Trifluoroacetic acid or trifluoroacetyl
Bzl Benzyl
t-Bu tert.-Butyl
HOBt Hydroxybenzotriazole
DMF Dimethylformamide
OD Optical density

I claim:

1. A peptide of the structure $$H\text{-}A_1\text{-}A_2\text{-}A_3\text{-}A_4\text{-}Gln\text{-}A_6\text{-}Lys\text{-}Val\text{-}A_9\text{-}A_{10}\text{-}NH_2 \quad (I)$$

in which $A_1$ = Leu
$A_2$ = Gly, Ser
$A_3$ = Pro
$A_4$ = Gly, Ser
$A_6$ = Ser
$A_9$ = Leu, Ile and
$A_{10}$ = Gly
and the salts thereof.

2. A peptide as claimed in claim 1, wherein the amino acids are in the L form.

3. A peptide as claimed in claim 1, wherein $A_1$ is in the D form.

4. A peptide as claimed in claim 1 having the formula
H-Leu-Gly-Pro-Gly-Gln-Ser-Lys-Val-Leu-Gly-NH₂
H-Leu-Ser-Pro-Ser-Gln-Ser-Lys-Val-Leu-Gly-NH₂
H-Leu-Gly-Pro-Gly-Gln-Ser-Lys-Val-Leu-Gly-NH₂
H-D-Leu-Gly-Pro-Gly-Gln-Ser-Lys-Val-Ile-Gly-NH₂ or
H-D-Leu-Gly-Pro-Gly-Gln-Ser-Lys-Val-Ile-Gly-NH₂.

5. A peptide of the structure $$H\text{-}A_1\text{-}A_2\text{-}A_3\text{-}A_4\text{-}Gln\text{-}A_6\text{-}Lys\text{-}Val\text{-}A_9\text{-}A_{10}\text{-}NH_2 \quad (I)$$

in which $A_1$ = Leu
$A_2$ = Gly, Ser
$A_3$ = Pro
$A_4$ = Gly, Ser
$A_6$ = Ser
$A_9$ = Leu, Ile and
$A_{10}$ = Gly,
or a salt thereof prepared by a process which comprises coupling together protected amino acid derivatives or peptide segments in solution or on a solid phase, and obtaining a peptide of the structure by elimination of the protective groups and, in the case of a solid phase, by elimination from the support resin.

6. A method for the quantification of blood coagulation factor XIII which comprises (a) mixing a substrate containing an effective amount of a peptide of the formula I in claim 1 with a sample solution containing factor XIII and (b) measuring the decrease in extinction.

7. A method for detecting reactions in which activated blood coagulation factor XII is produced, consumed or inhibited which comprises (a) mixing a substrate containing an effective amount of a peptide of the formula I in claim 1 with a sample solution containing factor XIII and (b) measuring the decrease in extinction.

* * * * *

UNITED STATES PATENT AND TRADEMARK OFFICE
CERTIFICATE OF CORRECTION

PATENT NO. : 5,049,506
DATED : September 17, 1991
INVENTOR(S) : Werner Stuber

It is certified that error appears in the above-identified patent and that said Letters Patent is hereby corrected as shown below:

Claim 4, column 6, line 31, change "$NH_2$or" to --$NH_2$ or--.

Claim 5, column 6, line 48, after "structure" insert --(I)--.

Claim 7, column 6, line 57, change "XII" to --XIII--.

Signed and Sealed this

Thirteenth Day of July, 1993

Attest:

MICHAEL K. KIRK

Attesting Officer    Acting Commissioner of Patents and Trademarks